United States Patent [19]

Griffith et al.

[11] Patent Number: 4,976,735
[45] Date of Patent: Dec. 11, 1990

[54] PROSTHETIC BLADDER AND METHOD OF PROSTHESIS IMPLANTATION

[76] Inventors: Donald P. Griffith, 5696 Longmont, Houston, Tex. 77056; Charles A. Homsy, 11562 Raintree, Houston, Tex. 77024

[21] Appl. No.: 341,734
[22] Filed: Apr. 20, 1989
[51] Int. Cl.⁵ ............................ A61F 2/04; A61F 2/02
[52] U.S. Cl. ........................................ 623/12; 600/30; 623/66
[58] Field of Search ............... 623/11, 12, 14, 1, 66; 128/DIG. 25; 600/29-31

[56] References Cited

U.S. PATENT DOCUMENTS

| | | | |
|---|---|---|---|
| 3,503,400 | 3/1970 | Osthagen et al. | 128/DIG. 25 |
| 3,866,247 | 2/1975 | Sparks | 623/1 |
| 3,953,897 | 5/1976 | Chevallet et al. | 623/12 |
| 3,988,782 | 11/1976 | Dardik et al. | 623/12 X |
| 4,044,401 | 8/1977 | Guiset | 623/12 |
| 4,228,550 | 10/1980 | Salkind | 623/12 X |
| 4,497,074 | 2/1983 | Rey et al. | 623/12 |
| 4,527,293 | 7/1985 | Eckstein et al. | 623/12 |

FOREIGN PATENT DOCUMENTS

| | | | |
|---|---|---|---|
| 2461627 | 7/1975 | Fed. Rep. of Germany | 623/12 |
| 2116838 | 7/1972 | France | 623/12 |
| 1296146 | 3/1987 | U.S.S.R. | 623/11 |

*Primary Examiner*—Ronald Frinks
*Attorney, Agent, or Firm*—Arnold, White & Durkee

[57] ABSTRACT

The present invention relates to a fixed volume prosthetic urinary bladder for use in a human being. The invention, more particularly, concerns a prosthetic urinary bladder comprising a vent channel having a removable cap and a urethral discharge valve. The present invention is intended for implantation in a human being such that the vent channel protrudes through the abdominal wall and the vent cap lies flush with the outer surface of the abdomen.

29 Claims, 3 Drawing Sheets

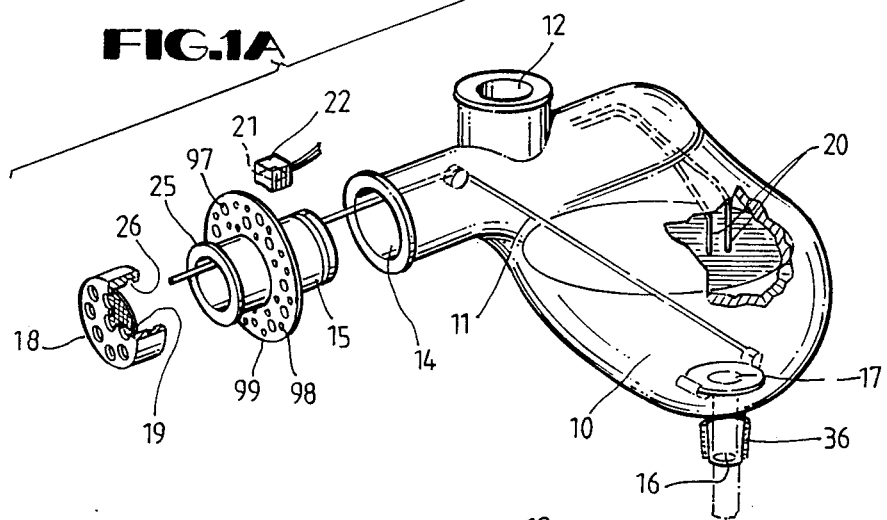
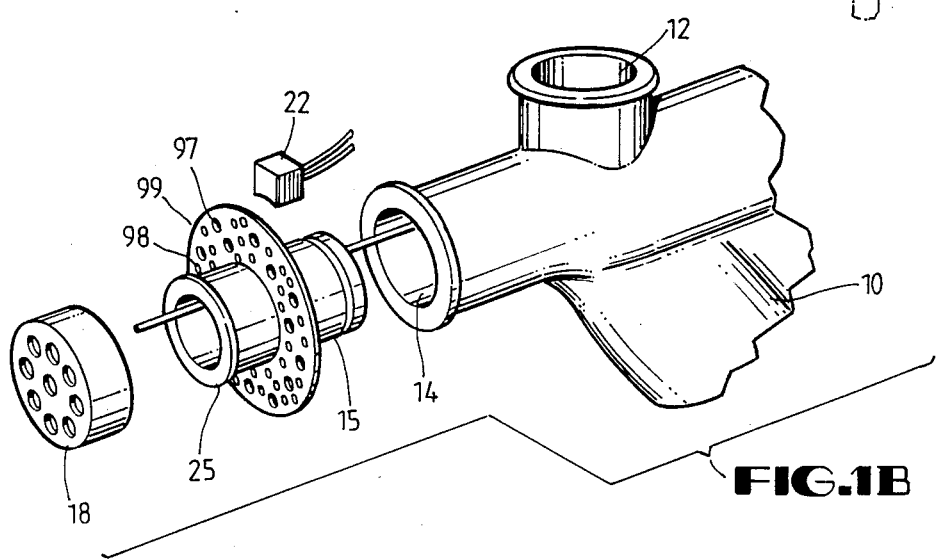
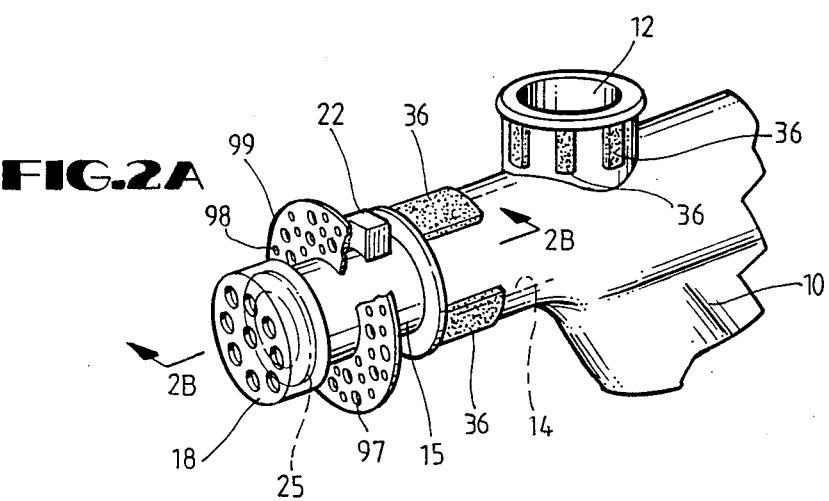

PROSTHETIC BLADDER AND METHOD OF PROSTHESIS IMPLANTATION

BACKGROUND OF THE INVENTION

1. Field of the Invention

The present invention relates to a fixed volume prosthetic urinary bladder for use in a human being. The invention, more particularly, concerns a prosthetic urinary bladder comprising (1) a reservoir or pouch, (2) an inlet channel, (3) a vent channel having a removable cap, (4) a urethral discharge channel, and (5) a volume sensing device and an alert system. Both the inlet channel and the discharge channel may contain replaceable valves.

The present invention also relates to the surgical procedure for implantation of the prosthetic devices, including a prosthetic bladder, in a human being. In the case of prosthetic bladder implantation, this procedure also entails anastomosing the inlet channel to the upper urinary tract (kidney, ureter or intestinal segment) and the discharge channel to the lower urinary tract (urethra).

2. Description of the Prior Art

Prosthetic urinary bladders have been known for many years. A typical bladder design is disclosed in U.S. Pat. No. 3,953,897 to Chevallet et al. Such a bladder comprises a flexible pouch which expands and contracts upon introduction and discharge of urine, two inlets channels and an outlet channel connectable to the urethra.

These conventional prosthetic bladders are plagued by many problems. First, the flexible walls of the pouch which expand and contract upon introduction and discharge of urine are known to undergo structural failures. These failures are due to the stress and fatigue zones resulting from the repeated expanding and contracting forces. These structural failures appear in the form of cracks and fractures often resulting in urinary leaks. A leaking prosthetic bladder is highly undesirable and can result in adverse medical consequences for the human patient in whom the bladder is implanted.

Another problem associated with conventional prosthetic urinary bladders is the buildup of calculi in the urinary tracts. The resulting encrustation from this calculi buildup causes a flow restriction and can often serve as a source of infection.

A widespread problem encountered by many patients having prosthetic bladder implants is incontinence. The involuntary discharge of urine resulting from incontinence can cause embarrassment to the patient as well as physical discomfort and damage to the patient's clothing.

Bacterial infection is another problem that has plagued many prosthetic devices, including artificial hearts. This infection is a result of bacterial colonization on the biomaterial surface. Such bacterial infection is believed to be a major or limiting factor on the long term use of many prosthetic devices, such as the artificial heart.

SUMMARY OF THE INVENTION

The present invention provides a fixed volume prosthetic bladder comprising a pouch or reservoir, a discharge channel, a urethral discharge valve located in or at the mouth of the discharge channel, a vent channel, and an inlet channel capable of being connected with an intestinal conduit or ureter. The discharge channel, vent channel and inlet channel are integrally formed in the reservoir. The invention is made of multiple materials that are biologically compatible with urine and organs surrounding the natural bladder.

The fixed volume nature of the reservoir requires an atmospheric vent to facilitate the filling and discharge of the bladder's liquid contents. The fixed volume design allows the reservoir to be constructed of rigid materials that will not be subjected to repeated stresses associated with expanding and contracting.

The vent channel on the present invention is intended to protrude through the abdominal wall of the patient in whom the invention is implanted. The vent channel may also be supported and fixed in position by an intracutaneous fixation device. A perforated cap is installed on the end of the vent channel such that the patient may reach down to his abdominal area and remove the cap. The perforated cap allows the bladder to vent during filling and discharge.

An air permeable, liquid water impermeable membrane is internally housed in the vent cap. This membrane acts as a "breathable" liquid barrier which prevents liquid from spilling out the vent channel when the patient is lying on his side or abdomen. It also prevents external liquid from entering the bladder during activities such as bathing.

The present invention contains a discharge valve located in or at the mouth of a discharge channel integrally formed in the lower portion of the pouch. The discharge channel or outlet is of a suitable size and material such that it can be coupled to the urethra. The discharge valve can be opened and closed by manipulating a valve actuator mounted on the inner or outer surface of the vent channel.

An inlet channel integrally formed in the top of the pouch is provided with the present invention to be surgically connected or anastomosed to the patient's intestinal conduit or ureter. This inlet channel will serve as the pathway for the introduction of urine into the prosthetic bladder. A replaceable, non-refluxing valve, commonly known as a check valve, may be incorporated into the inlet channel to prevent reflux of urine from the reservoir into the kidney.

The discharge valve actuator may be a signal transmitter that gives off a signal that is received by a signal receiver mounted adjacent to the discharge valve. The signal receiver is configured to actuate an electromechanical servomechanism to open and close the valve. Alternatively, the actuator may be a mechanical device such as a squeeze bulb hydraulically coupled to the discharge valve or a lever mechanically coupled to the discharge valve via a linkage mechanism. The linkage mechanism may be a cable.

A means for controlling calculi buildup and encrustation in the prosthetic bladder and associated urinary tracts is provided by the present invention. It is well known that many compounds such as potassium citrate, acetohydroxamic acid, and other chemicals and pharmaceuticals inhibit crystallization of poorly soluble calcium and magnesium salts. It is also well known that various pharmacological and chemical agents such as antibiotics, or metallic compounds inhibit the growth of or kill microbes. The patient in whom the invention is implanted can add compounds in solid tablet or solution form to his prosthetic bladder in order to prevent bacterial growth and/or encrustation. The addition of these chemicals is easily accomplished by removing the perforated cap and introducing the chemicals into the vent channel opening located in the patient's abdomen.

The present invention also comprises a level or volume sensor located in the pouch which gives off a perceivable level or volume signal when the amount of urine in the prosthetic bladder reaches a predetermined level or volume. The perceivable signal may be an audio signal, such as an alarm, or a tactile signal, such as a vibration or electric shock. The level signal will alert the patient that it is necessary to discharge urine from the bladder, thus eliminating incontinence problems encountered in prior art prosthetic bladders.

The present invention also comprises an inert, porous, flexible, prosthetic material to effect watertight, bacterial resistant, fibroblastic bonding of the reservoir to (a) the upper urinary tract, including the kidney, ureter, or intestinal conduit, (b) the lower urinary tract or urethra, (c) the muscles and fascia of the abdominal wall, (d) the normal pelvic tissues, including fat, and muscle, and (e) the skin.

Watertight, bacterial resistant bonding of the prosthesis is critical to its success inasmuch as intraluminal and extraluminal infection may promote failure of the prosthesis. Such bonding resists this bacterial infiltration which has led to bacterial infection in many prior art prosthetic devices.

This invention also relates to a surgical procedure for implanting prosthetic devices, including the prosthetic urinary bladder of the present invention, into a human patient. This procedure takes place in multiple phases which facilitate the bacterial resistant bonding of the prosthesis to the surrounding areas of the body as discussed above. This multi-phased surgical implantation procedure is applicable to prosthetic urinary bladders, as well as other prosthetic devices.

In Phase I the deactivated or defunctionalized device is implanted and anastomotic unions are made with the prosthesis and the surrounding internal tissues or organs. The prosthetic device remains in this phase for several weeks or months while fibroblastic bonding occurs. Following fibroblastic bonding the prosthesis is more resistant to intraluminal and extraluminal bacterial infection.

In Phase II of the surgical procedure, the skin union is effected with the prosthesis. In the Phase III of the procedure, the union (anastomosis) of other organs to the prosthesis is effected. In the case of a prosthetic urinary bladder, the bodily organs are the upper urinary tract.

Bacterial infection from normal skin flora is the greatest risk of device failure. The probability of such failure is greatly reduced by the phased implantation of the prosthesis and utilization of the porous, flexible, inert bonding material that enhances fibroblastic bonding of the prosthesis.

BRIEF DESCRIPTION OF THE DRAWINGS

FIG. 1A is an exploded isometric view of the prosthetic bladder.

FIG. 1B is an enlarged exploded isometric view of the upper portion of the prosthetic bladder shown in FIG. 1A.

FIG. 2A is an isometric view depicting the vent channel, endpiece, and vent cap in an assembled configuration.

DETAILED DESCRIPTION OF THE PREFERRED EMBODIMENTS

Figure 2B:
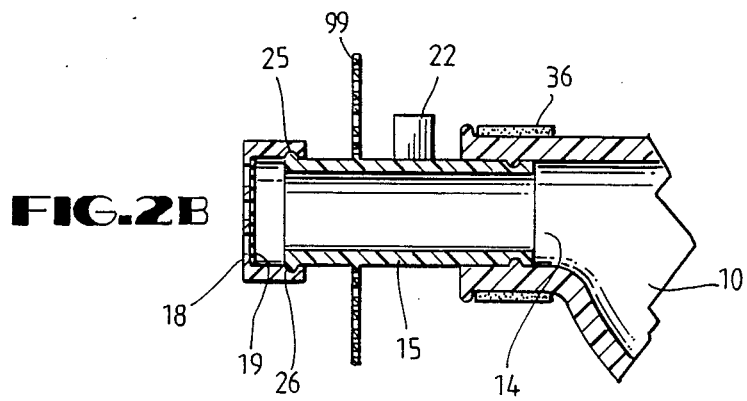
FIG. 2B is a cross-sectional view of the vent channel, endpiece, fixation device and vent cap of the type depicted in FIG. 2A.

Referring to FIG. 1, the prosthetic bladder is comprised of a fixed volume reservoir 10 having an inlet channel 12 integrally formed in the top, a discharge channel 16 integrally formed in the bottom, and a vent channel 14 integrally formed in the front of said reservoir.

As illustrated in FIGS. 1 and 2, the vent channel 14 comprises a removeable endpiece 15 having a first male end insertable in the end of said vent channel 14. Tissue bonding buttresses 36, as shown in FIG., 2, lie on the outer surface of vent channel 14. These buttresses are made from flexible, inert, porous materials which promote tissue growth. Such materials are described in U.S. Pats. No. 3,992,725 and 4,576,608 to Homsy.

Improved fixation of the prosthetic bladder may be achieved by using an intracutaneous fixation device. In a preferred embodiment of the invention, an intracutaneous fixation device 99 slideably engages the outer surface of vent channel 14. In a preferred embodiment, as depicted in FIGS. 1 and 2, the intracutaneous fixation device 99 is a flexible flange, constructed of porous material. The porosity of intracutaneous fixation device 99 is enhanced by the multiplicity of micropores 98 and macropores 97 which permeate intracutaneous fixation device 99. The micropores 98 are depicted in FIGS. 1A, 1B, 2A, 2B and 3 for illustrative purposes only. The miropores 98 are actually of a size too small to be visible to the naked eye.

Intracutaneous fixation device 99 is constructed of a tissue ingrowth promoting flexible material which can be trimmed by a surgeon using common surgical tools. The flexing properties of intracutaneous fixation device 99 give it increased resistance to extrusion failure, a problem which has commonly occurred in stiffer fixation devices such as stiff flanges.

A perforated cap 18 is designed to tightly fit over the second male end of the endpiece 15. This tight fit may be accomplished via a snap fit arrangement wherein a groove 26 on the inner wall of the perforated cap 18 snaps over a lip 25 on the second end of the endpiece 15. This snap fit is intended to provide a liquid tight seal between the perforated cap 18 and the endpiece 15. Such a seal may also be accomplished by other mechanical coupling arrangements such as a screw on cap.

The assembled configuration of the perforated cap 18, endpiece 15, and vent channel 14 is depicted in FIG.

2. The perforated cap 18 comprises an air permeable, water impermeable membrane 19 internally housed in cap 18. The membrane is preferably made from a tetrafluoroethylene polymer material such as that sold under the trademark GORE-TEX or other air permeable, water impermeable material.

Figure 4:
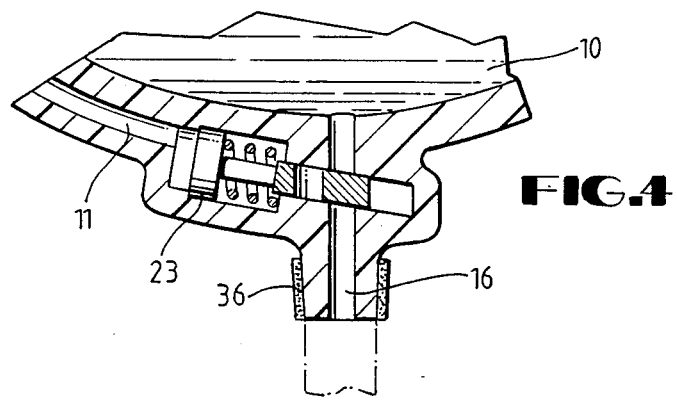
FIG. 4 is a cross-sectional side view of a discharge valve and hydraulic actuator of the type depicted in FIG. 3.

A discharge valve 17 is installed in or at the mouth of discharge channel 16 as depicted in FIGS. 1 and 4, respectively. This discharge valve 17 may be manually opened and closed through the use of a linkage mechanism 11. In the embodiment depicted in FIG. 1, the linkage mechanism 11 is a cable.

Figure 8:
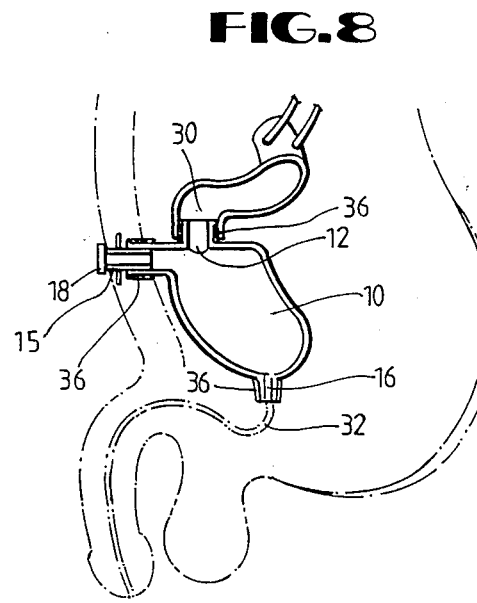
FIG. 8 is a side view of the present invention implanted in a patient after the final step in the surgical implantation procedure.

Discharge channel 16 also contains tissue bonding buttresses 36 on its outer surface as shown in FIG. 8. These buttresses are of the same type as those applied to the external surface of vent channel 14. The outer surface of inlet channel 12 also contains tissue bonding buttresses 36, as shown in FIG. 2.

Figure 3:
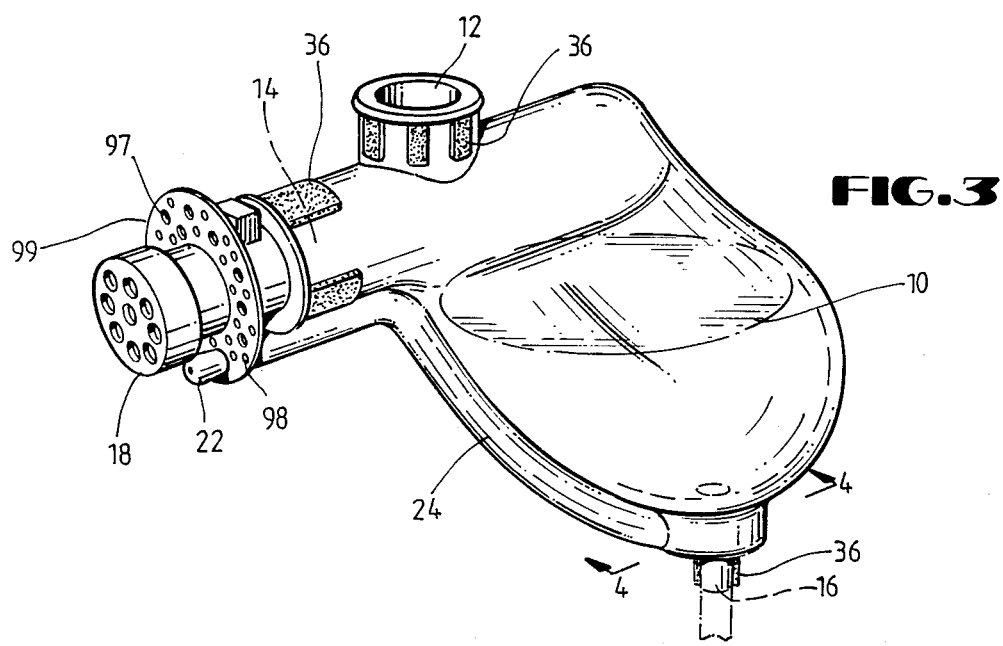
FIG. 3 is an isometric view of another embodiment of the invention comprising a hydraulic valve actuator mechanism externally mounted on the pouch and vent channel and enclosed in a casing.

Another embodiment of the discharge valve 17 and linkage mechanism 11 is depicted in FIGS. 3 and 4. Referring to FIG. 4, a hydraulically actuated discharge valve 17 is located in discharge channel 16. A linkage mechanism comprising hydraulic line 11 and piston 23 couples discharge valve 17 to valve actuator 22. Valve 17 may be actuated by a hydraulic fluid pressurization device such as a squeeze bulb. As shown in FIG. 3, valve actuator 22 is a squeeze bulb. The hydraulic line 11 is externally mounted on reservoir 10 and vent channel 14 and enclosed in linkage casing 24.

Figure 5:
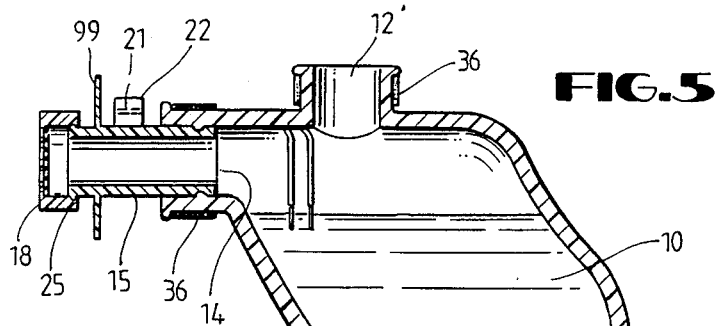
FIG. 5 is a cross-sectional side view of another embodiment of the prosthetic bladder having a radio signal actuated discharge valve.

Referring to FIG. 5, discharge valve 17 may also be opened and closed by radio signal actuation. The valve actuator 22 is a signal transmitter capable of transmitting a signal that is received by signal receiver 28. Signal receiver 28 is coupled to electromechanical servomechanism 27. Electromechanical servomechanism 27 is capable of opening and closing discharge valve 17 upon receipt of radio signals from actuator 22.

Referring to FIGS. 1 and 5, level sensors 20 are internally mounted in the upper portion of reservoir 10. In a preferred embodiment, these level sensors are two electrodes having a voltage potential between them. Other level sensors such as a float and lever switch or a radioisotopic source and receiver may also be used.

Electrodes 20 are placed at a predetermined level in reservoir 10. When the urine level in reservoir 10 reaches this predetermined level the circuit is completed between the electrodes 20. This circuit completion triggers a level alarm 21 which is electrically coupled to level sensors 20. In a preferred embodiment, level alarm 21 has a time delayed actuation to avoid false alarms due to urine splashing.

In a preferred embodiment, level alarm 21 is a microchip which gives off an audible signal in response to an electrical input. This microchip is housed in the same casing as valve actuator 22. The level alarm may also be tactile signal such as an electric shock or a vibration.

The uniqueness of the present invention is better understood in light of the surgical procedures used to implant this device and its interaction with the biological medium surrounding it. In a method embodiment, the present invention further comprises the surgical procedure used to implant the prosthetic urinary bladder described above.

Figure 6:
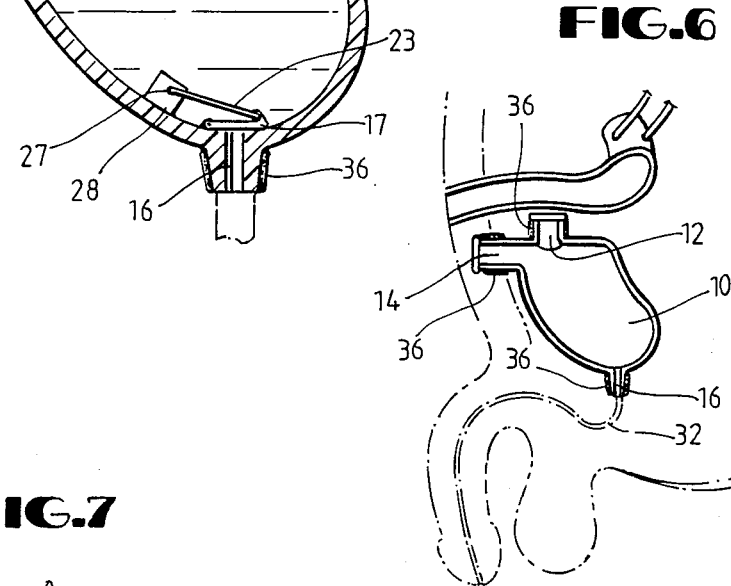
FIG. 6 is a side view of the present invention implanted in a patient after the first step in the surgical implantation procedure.
Figure 7:
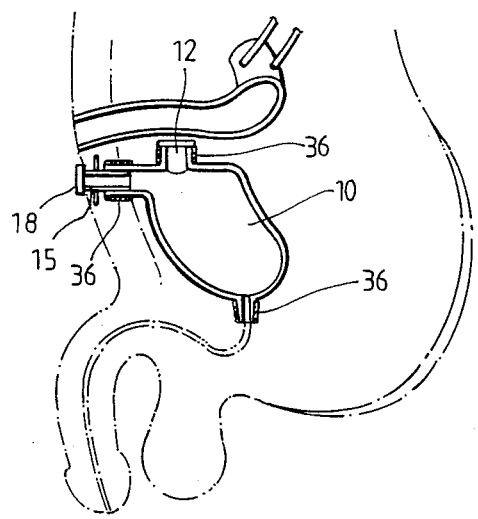
FIG. 7 is a side view of the present invention implanted in a patient after the second step in the surgical implantation procedure.

These procedures are illustrated in FIGS. 6–8 in a male patient. It is understood that these procedures are equally applicable to a female patient. In the first surgical step as shown in FIG. 6, a defunctionalized prosthetic bladder is implanted in the patient's pelvis and anastomosed to the patient's urethra 32. The vent channel 14 of the prosthetic bladder is pointed toward the inner abdominal wall of the patient.

Intracutaneous fixation device 99 may be slideably affixed to vent channel 14 prior to implantation of the prosthetic bladder. Alternatively, intracutaneous fixation device 99 may be slideably positioned onto vent channel 14 during the implantation of the prosthetic bladder in the patient.

In a preferred embodiment where intracutaneous fixation device 99 is a flange, sutures may used to connect the flange to buttresses 36 intraoperatively. At the time of implantation, the outer diameter of intracutaneous fixation device 99 will be trimmed to correspond to the anatomical requirements of the tissue in which it will be located.

Concurrently with the installation of this prosthetic bladder, a nonrefluxing intestinal conduit 30 is created in the patient's body.

The implanted prosthesis is given a period of at least several days to allow fibroblastic fixation of tissue surrounding the prosthesis to the intracutaneous fixation device 99 and to the porous, inert, flexible buttresses 36 that are bonded on the external surface of the reservoir as detailed in FIG. 6. In some cases this fixation period takes several weeks.

After the fibroblastic fixation to the tissue bonding buttresses 36 occurs, a second surgical procedure, as shown in FIG. 7, is performed. In this procedure a plug of abdominal skin is removed to access the end of the vent channel 14. A removable endpiece 15 may be externally coated with a tissue ingrowth promoting porous material such as those described in U.S. Pat. Nos. 3,992,725 and 4,576,608 to Homsy. The material described in the '725 patent is sold under the trademark PROPLAST. Other materials may also be suitable as an external coating for endpiece 15 thereby creating a cosmetically attractive, watertight, tissue/prosthesis bond that is resistant to bacterial infection. These materials include woven polyurethane, polyester or polytetrafluoroethylene as well as materials sold under the trademarks DACRON and GORE-TEX.

Endpiece 15 is inserted into the end of the vent channel 14. Endpiece 15 is of sufficient length such that the outer male end extends to or beyond the outer surface of the patient's abdomen.

The perforated cap 18 with the internally housed membrane 19 is then installed on the outer end of the endpiece 15. The cap 18 fits on tightly in a snug fit or screw on type arrangement. The prosthesis remains defunctionalized until skin and abdominal wall tissue heal around the endpiece 15 and the vent cap 18. It is envisioned that skin will grow into the PROPLAST on the outer surface of the endpiece 15, if endpiece 15 is externally coated with PROPLAST.

The performance of the defunctionalized prosthesis may be repeatedly tested with water or with infected urine with and without the additions of pharmaceuticals or chemicals to thoroughly evaluate the functionability and integrity of the prosthesis.

In a third surgical procedure, as shown in FIG. 8, the intestinal conduit 30 is coupled or anastomosed to the inlet channel 12 located in the top of the prosthesis. The discharge channel 16 and the vent channel 14 are of sufficient diameter to permit installation and removal of the urethral discharge valve 17 and an inlet anti-reflux valve by endoscopic manipulation. Upon completion of the intestinal conduit anastomosis, the prosthetic bladder is ready for normal operation in the patient.

Many modifications and variations may be made in the embodiments described herein and depicted in the accompanying drawings without departing from the concept of the present invention. Accordingly, it is clearly understood that the embodiments described and illustrated herein are illustrative only and are not intended as a limitation upon the scope of the present invention.

What is claimed is:

1. A prosthetic bladder suitable for implantation in a human patient, comprising:
   a fixed volume reservoir made of material that is biologically compatible with organs surrounding the natural bladder;
   an inlet channel integrally formed in the top of said reservoir;
   a vent channel integrally formed in said reservoir and extending sufficiently outward from the upper front portion of said reservoir to reach through the abdominal wall of the patient in which said bladder is to be implanted;
   a removable perforated cap affixed on the end of said vent channel;
   a discharge channel integrally formed in the bottom of said reservoir
   a discharge valve located in said discharge channel; and
   a valve actuator coupled to said discharge valve.

2. The prosthetic bladder of claim 1 wherein said cap comprises an internally housed air permeable water impermeable membrane.

3. The prosthetic bladder of claim 2 further comprising a linkage mechanism coupled at a first end to said discharge valve and coupled at a second end to said valve actuator.

4. The prosthetic bladder of claim 3 further comprising a linkage casing externally mounted on said reservoir and vent channel, enclosing said linkage mechanism.

5. The prosthetic bladder of claim 2 wherein said valve actuator is a squeeze bulb.

6. The prosthetic bladder of claim 2 wherein said valve actuator is a signal transmitter.

7. The prosthetic bladder of claim 6 further comprising:
   a signal receiver mounted adjacent to said discharge valve; and
   an electromechanical servomechanism coupling said signal receiver to said discharge valve.

8. The prosthetic bladder of claim 2 wherein said membrane is made from a tetrafluoroethylene polymer.

9. The prosthetic bladder of claim 1 wherein said vent channel comprises a removable endpiece having a first male end insertable in said vent channel and a second male end coupled to said cap.

10. The prosthetic bladder of claim 9 wherein the outer surface of said removable endpiece is coated with a tissue ingrowth promoting flexible coating.

11. The prosthetic bladder of claim 1 further comprising an intracutaneous fixation device slideably engaging the outer surface of said vent channel.

12. A prosthetic bladder suitable for implantation in a human patient, comprising:
    a fixed volume reservoir made of material that is biologically compatible with organs surrounding the natural bladder;
    an inlet channel integrally formed in the top of said reservoir;
    a vent channel integrally formed in said reservoir and extending sufficiently outward from the upper front portion of said reservoir to reach through the abdominal wall of the patient in which said bladder is to be implanted;
    a removable perforated cap affixed on the end of said vent channel;
    a discharge channel integrally formed in the bottom of said reservoir
    a discharge valve located in said discharge channel;
    a valve actuator coupled to said discharge valve;
    a level sensor internally mounted in the upper portion of said reservoir; and
    a level alarm electrically coupled to said level sensors such that said level alarm generates a perceivable signal when said level sensor senses a predetermined liquid level in said reservoir.

13. The prosthetic bladder of claim 12 wherein said perceivable signal is an audio signal.

14. A prosthetic bladder suitable for implantation in a human patient, comprising:
    a fixed volume reservoir made of material that is biologically compatible with organs surrounding the natural bladder;
    an inlet channel integrally formed in the top of said reservoir;
    a vent channel integrally formed in said reservoir and extending sufficiently outward from the upper front portion of said reservoir to reach through the abdominal wall of the patient in which said bladder is to be implanted;
    a removable perforated cap affixed on the end of said vent channel;
    a discharge channel integrally formed in the bottom of said reservoir;
    a discharge valve located in said discharge channel;
    a valve actuator coupled to said discharge valve;
    a volume sensor internally mounted in the upper portion of said reservoir; and
    a volume alarm electrically coupled to said volume sensors such that said volume alarm generates a perceivable signal when said volume sensor senses a predetermined liquid volume in said reservoir.

15. The prosthetic bladder of claim 14 further comprising a flexible flange slideably engaging the outer surface of said vent channel.

16. The prosthetic bladder of claim 15 wherein said flange comprises a multiplicity of micropores and macropores.

17. The prosthetic bladder of claim 14 wherein said perceivable signal is an audio signal.

18. A prosthetic bladder suitable for implantation in a human patient, comprising:
    a reservoir having an inlet, an outlet and a vent channel;
    a removable perforated cap affixed on the end of the vent channel; and
    a discharge valve installed in the outlet of said reservoir.

19. The prosthetic bladder of claim 18, further comprising an air permeable, water impermeable membrane internally housed in said cap.

20. The prosthetic bladder of claim 19, further comprising:
    a valve actuator mounted on the vent channel of said reservoir; and a hydraulic linkage mechanism linking said valve actuator to said discharge valve.

21. The prosthetic bladder of claim 20 wherein said valve actuator is a hydraulic fluid pressurization device.

22. The prosthetic bladder of claim 20 wherein said valve actuator is a signal transmitter.

23. The prosthetic bladder of claim 22 further comprising:
    a signal receiver mounted adjacent to said discharge valve; and
    an electromechanical servomechanism coupling said signal receiver to said discharge valve.

24. The prosthetic bladder of claim 20 further comprising:
    a level sensor internally mounted in the upper portion of said reservoir; and
    a linkage mechanism linking said valve actuator to said discharge valve.

25. A method for implanting a prosthesis in a human patient comprising the steps of:
    surgically implanting a deactivated prosthesis in the patient during a first surgical procedure;
    making anastomotic unions with the prosthesis and the surrounding internal body regions during the first surgical pocedure;
    allowing the deactivated prosthesis to remain in the patient for a period of several weeks during which time fibroblastic bonding occurs; and
    making anastomotic union between the prosthesis and the bodily organ to which it is coupled during a second surgical procedure.

26. The method of claim 25 further comprising the steps of:
    testing the deactivated prosthesis to ensure its functional operability; and
    activating the prosthesis.

27. A method for implanting a prosthetic urinary bladder having a vent channel, an inlet channel, and a discharge channel in a human patient comprising the steps of:
    implanting a defunctionalized prosthetic bladder in the patient's pelvic cavity;
    coupling the discharge channel of the prosthesis to the patient's urethra;
    allowing the defunctionalized prosthesis to remain in the patient's body for a period of at least several days, during which time fibroblastic fixation takes place;
    surgically removing a plug of abdominal skin at a position on the patient's abdomen located over the opening of the prosthesis vent channel;
    inserting a cylindrical endpiece of sufficient length into the vent channel such that the outer end of the endpiece extends beyond the outer surface of the patient's abdomen;
    waiting a sufficient period of time for the skin and tissue in the vicinity of the endpiece to heal; and
    coupling the inlet channel of the prosthesis to the patient's intestinal conduit.

28. The method of claim 27 further comprising the steps of:
    endoscopically installing a discharge valve in the discharge channel of the prosthesis; and
    installing a perforated cap on the outer end of the endpiece.

29. A prosthetic bladder suitable for implantation in a human patient, comprising:
    a fixed volume reservoir having an inlet, an outlet and a vent channel integrally formed with said reservoir,
    a removable perforated cap affixed on the end of the vent channel; and
    a discharge valve installed in the outlet of said reservoir.

* * * * *